United States Patent [19]
Weinstein et al.

[11] Patent Number: 5,007,419
[45] Date of Patent: Apr. 16, 1991

[54] INHALER DEVICE

[76] Inventors: Allan Weinstein, 9205 Pegasus Ct., Potomac, Md. 20854; Robert Weinstein, 6903 Alderley Way, West Bloomfield, Mich. 48033

[21] Appl. No.: 395,776
[22] Filed: Sep. 25, 1989
[51] Int. Cl.$^5$ .................................... A61M 11/00
[52] U.S. Cl. ........................ 128/200.23; 128/200.14
[58] Field of Search ............... 128/200.14, 200.23, 128/200.19, 203.12, 203.14, 205.21; 222/135, 145, 402.12

[56] References Cited

U.S. PATENT DOCUMENTS

| | | | |
|---|---|---|---|
| 398,327 | 2/1889 | De Vars | 128/200.14 |
| 3,012,694 | 12/1961 | Johnston | 128/205.21 |
| 3,184,115 | 5/1965 | Meshberg | 128/200.23 |
| 3,451,593 | 6/1969 | Dillarstone | 222/135 |
| 3,704,725 | 12/1972 | Marand | 222/145 |
| 3,908,868 | 9/1975 | Peirish, Jr. | 222/145 |
| 3,923,202 | 12/1975 | Riccio | 222/145 |
| 3,926,343 | 12/1975 | Kleiner | 222/145 |
| 4,261,481 | 4/1981 | Speer | 222/135 |
| 4,593,836 | 6/1986 | Lilienthal | 222/135 |
| 4,791,149 | 12/1988 | Pocknell | 222/135 |
| 4,887,591 | 12/1989 | Okumura | 128/205.21 |

FOREIGN PATENT DOCUMENTS 1153781  9/1963  Fed. Rep. of Germany ........................ 128/205.21

Primary Examiner—Aaron J. Lewis
Attorney, Agent, or Firm—Hopgood, Calimafde, Kalil, Blaustein & Judlowe

[57] ABSTRACT

An inhaler device that is able to house multiple removable canisters of medication. The inhaler device may also have extendable and retractable outlet nozzles, spacer devices, a cover and assorted cap designs to ensure proper use of the device and application of the medication.

11 Claims, 2 Drawing Sheets

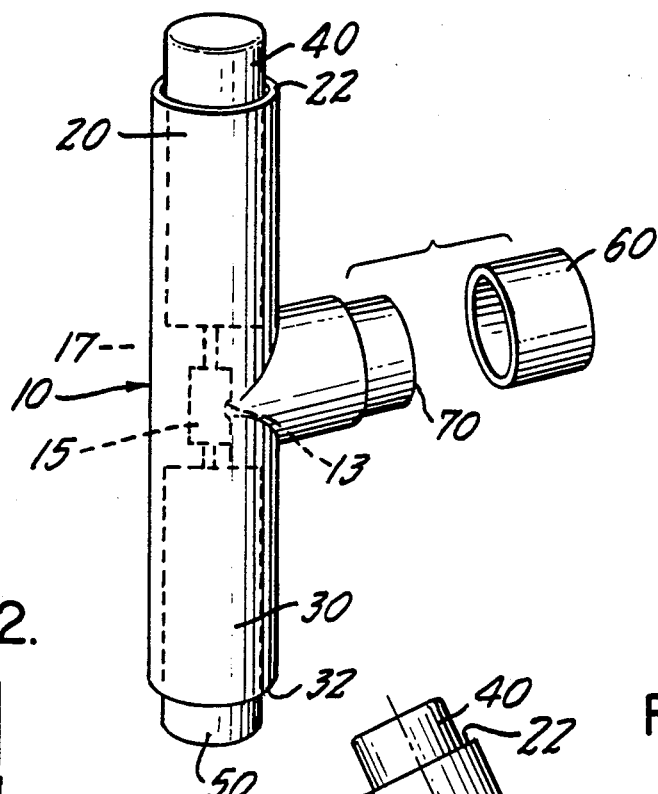
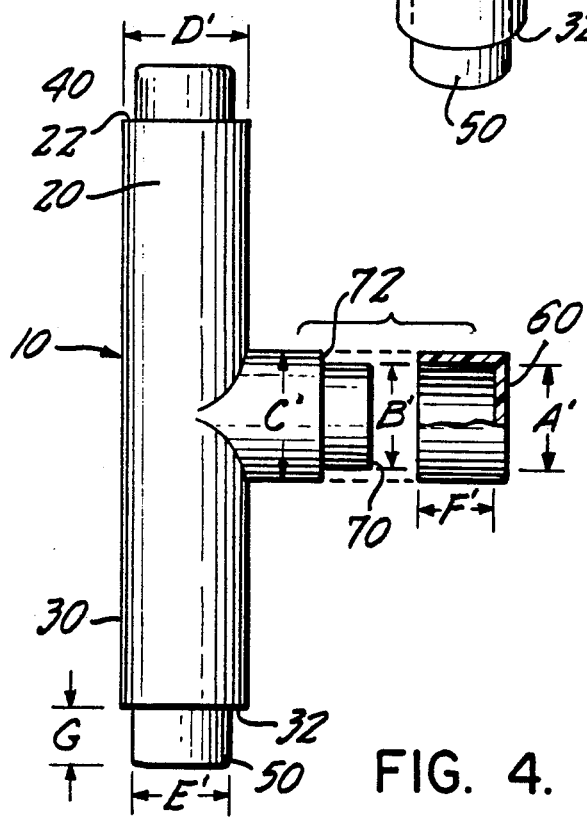
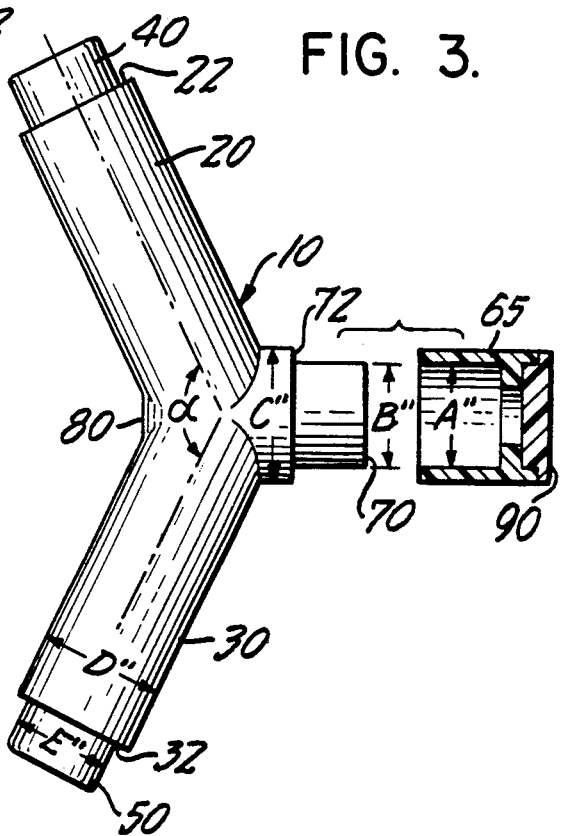
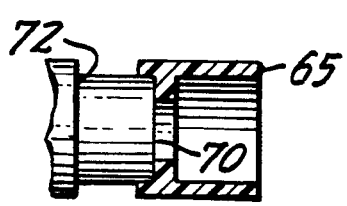

FIG. 5.
FIG. 6.
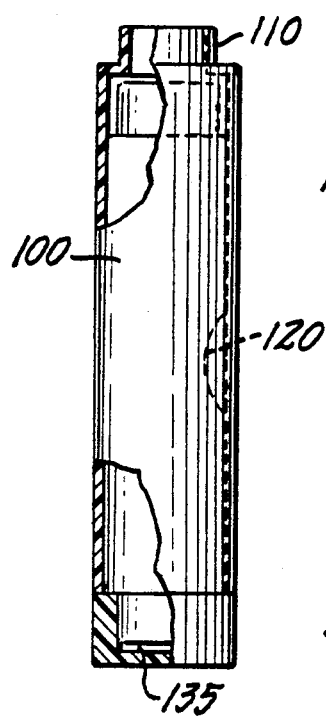
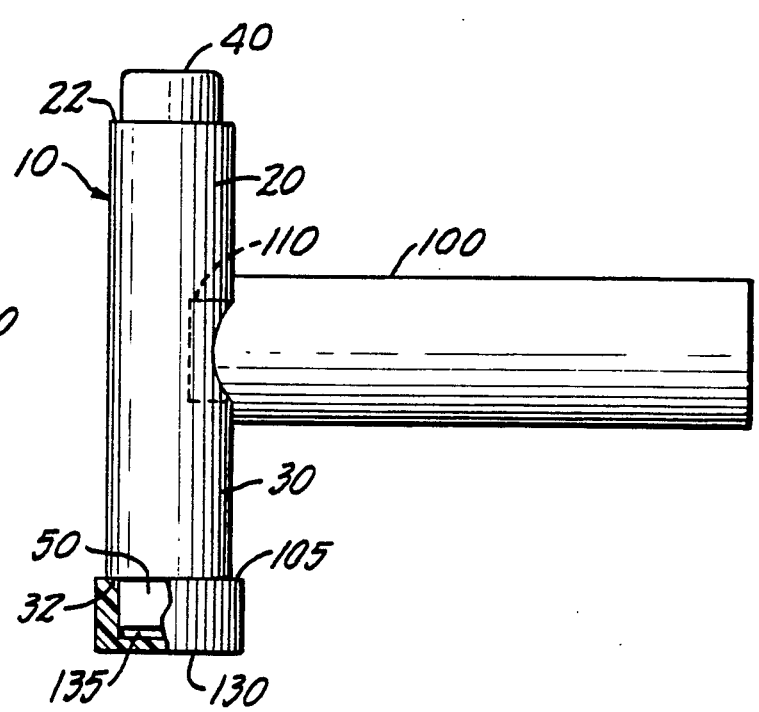
FIG. 7.
FIG. 8.
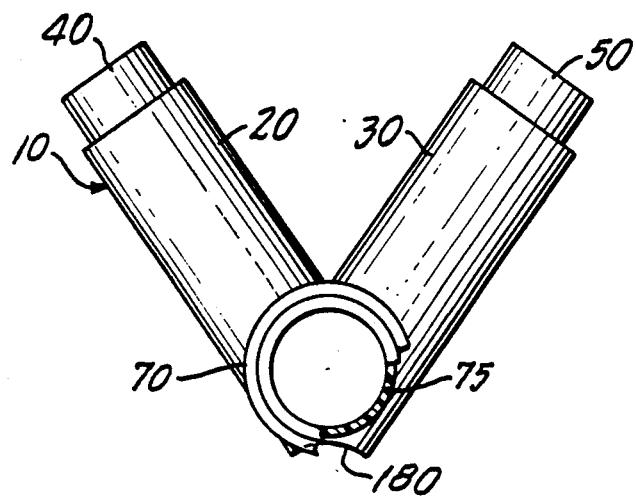
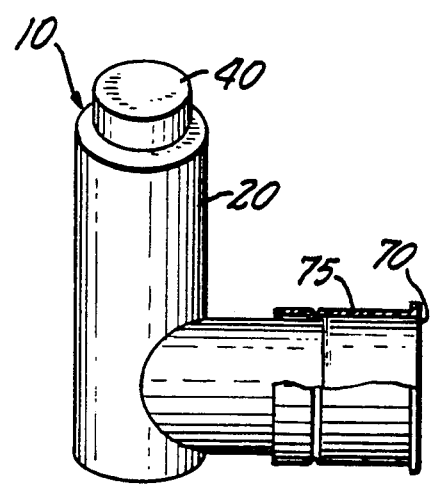

INHALER DEVICE

The present invention relates to an inhaler device for dispensing medication.

Ailments such as asthma and other obstructive lung diseases are frequently treated effectively by topical inhalation of medication. Inhalational application offers a rapid delivery of medication directly to the site of the problem—the interior of the bronchial tree. In contrast, oral or parental medication dosages require systemic absorption and systemic distribution of medication in order for a fraction of that medication to get to the desired site and produce a therapeutic benefit.

Because inhalational application is direct, smaller amounts of medication are required to produce the same benefit than amounts required when the medication is given orally or parentally. The undesirable side effects of currently used oral beta-adrenergic agonists and oral corticosteroid medications include tremor, rapid or possibly irregular heart beats, and gastrointestinal upset for the former; and increased blood sugar, high blood pressure, weight gain, cataract formation, calcium mobilization from bones (osteoporosis) and growth retardation in children for the latter. These and other risks can be sharply reduced by minimizing systemic absorption and utilizing the inhaled route for administration of these medications.

Single canister inhalers, containing only one medication, are presently available for the treatment of obstructive lung disease. It is frequently desirable, however, to utilize more than one inhaled medication. Combined regimens of inhaled medication can be tailored to produce desired effects. It is thus a desirable treatment regimen to combine one medication that provides immediate relief with a second dose of medication that produces long term (preventive) help.

For example, an immediate acting bronchodilating agent of the beta-adrenergic type (adrenaline-like) might be used first to dilate the spastic bronchial tree, which would then be followed by an inhaled slower acting corticosteroid which can settle inflammation over a longer period of time. Alternative strategies might be to follow an immediate acting bronchodilator with a prophylactic agent such as cromolyn sodium, a medication which prevents the further release of mediators that induce bronchospasm. Yet another strategy might be to use two bronchodilators that operate by different mechanisms sequentially in order to derive synergistic bronchodilitation, yet minimize side effect by virtue of small dosages of each rather than a larger dose of one alone.

An existing problem with inhalers on the market today is that patients are more motivated and likely to use the medication which offers immediate relief but need more encouragement to regularly utilize a second, less immediate acting (albeit more sustained or prophylactic) preparation. Proper treatment frequently entails consistent use of both. Another significant existing problem with current inhalers concerns their technique and use. Most inhaler users place the inhaler in their mouth causing the aerosol to hit the oral mucous membranes and the back of the mouth thus forming droplets which are swallowed—as opposed to an inhaled mist which reaches the lungs. To some extent, this incorrect use of the inhaler can be directly attributed to the existing design of inhalers on the market today.

These significant problems and insufficiencies associated with standard inhalers are still present today. Even though attempts may have been made to overcome the foregoing difficulties and disadvantages none as far as we are aware, have succeeded or have been entirely successful.

SUMMARY AND OBJECTS OF THE INVENTION

The inhaler device of the present invention comprises a housing having a first and second chamber, each of which has an internal compartment to house a removable canister of medication. The housing also has at least one common outlet nozzle which is in fluid communication with the canisters of medication via a communication channel which releases the pressurized medication and directs the aerosol spray out the common outlet nozzle. The inhaler device may also require a removable cap which can cover either the outlet nozzle or one of the exposed canisters of medication.

It is an object of the present invention to overcome the above described difficulties and disadvantages associated with existing inhalers and asthma medication techniques by incorporating more than one medication into a single, convenient inhalational treatment device.

It is a further object of the present invention to provide an inhaler device that is able to disperse more than a single medication with optional spacer devices.

The invention provides different housing configurations in which the canisters can be arranged on the same axis or angled in various configurations. The inhaler of the invention includes a removable cap which fits over both the outlet nozzle and can be placed over either of the canisters to form a thumb-hold when the other non-covered canister is activated. The inhaler of this invention may include either a common outlet nozzle or separate outlets for releasing the aerosol spray.

The invention provides for both an extended mouthpiece-spacer to optimize delivery of the aerosol, or an extendable and retractable outlet nozzle. The invention also provides the dual use of a cover to both protect the inhaler and to be removed and inserted as an extended outlet nozzle during use.

BRIEF DESCRIPTION OF THE DRAWINGS

FIG. 1 is an isometric view of an inhaler device and removable cap according to an embodiment of the present invention;

FIG. 2 is a side view, partly in cross-section of the inhaler device of FIG. 2;

FIG. 3 is a side view of another embodiment of the invention which include angled inhaler and extendable cap;

FIG. 4 is a side view of the removable cap of the embodiment of FIG. 3 in an extended position;

FIG. 5 depicts an inhaler device according to a third embodiment of the present invention;

FIG. 6 is an uncovered inhaler device of the embodiment of FIG. 5 with the cover removable and attachable as the outlet nozzle; and FIGS. 7 and 8 depict another embodiment of the present invention.

DETAILED DESCRIPTION OF THE PREFERRED EMBODIMENTS

Broadly considered, the present invention provides an inhaler device that contains a housing having separate compartments for two or more removable canisters of medication and at least one outlet nozzle to disperse the aerosol spray from the manually operated canister.

The embodiment of the invention illustrated in FIGS. 1 and 2 includes a housing 10 that has two cylindrical chambers 20, 30 which receive removable canisters 40, 50 which contain different medications, one for immediate relief and a second for long term preventative treatment. The housing has a common outlet nozzle 70 which has fluid communication with the interior of the housing. The housing also contains a communication channel 15 for releasing the pressurized medication through an exit nozzle 13 and allowing the aerosol spray to pass to and through the outlet nozzle 70. The canisters of medication 40, 50 are opposingly attached to the communication channel 15 via canister needles 17.

A removable cap 60 is snugly fitted over the output nozzle 70 and has an inner diameter dimension of A′. The outlet nozzle 70 has an outer diameter of B′ and the removable canisters 40, 50 have each a diameter of E′. The dimensions are such that A, is larger than both B′ and E′, so that the cap 60 can fit over these surfaces. Dimensions C′ and D′ are larger than B′ and E′, respectively so as to form ledges 72, 32 and 22.

When in the fitted position, the cap 60 of the inhaler of FIG. 1 remains over the common outlet nozzle 70. To use the device the cap 60 is removed from the outlet nozzle 70 and placed over the canister of medication 40 or 50 that will not be used. Then by applying manual pressure between the uncapped canister and the capped canister, the uncapped canister is forced down towards the communication channel 15 causing the canister needle 17 to release stored pressurized medication as an aerosol spray through the communication channel 15 and out the exit nozzle 13 towards and through the outlet nozzle 70.

To disperse a dose of the other medication from the other canister, the user merely switches the cap 60 to cover the previously uncovered canister, thereby allowing the unused canister to be uncapped and free to be depressed towards the communication channel 15 causing a release of its contained medication.

The cap 60 has an interior height of F′ which is greater than the distance G′ between the top of the canister 40, 50 and the ledges 22, 32. This dimensional difference is important so that when the cap covers a canister and pressure is applied to the cap, the canister which it covers is not forced into the communication channel 15 causing an undesired release of medication.

The common outlet nozzle 70 may be extendable and retractable. The advantages of an extendable nozzle are to keep the device farther away from the mouth during use, so that the medication will remain as an aerosol mist as opposed to hitting the back of the mouth and forming droplets.

The embodiment of the invention illustrated in FIG. 3 is similar to that of FIGS. 1 and 2 with certain significant differences. As opposed to FIGS. 1 and 2, the canisters of FIG. 3 are not positioned axially end to end in the housing, but are angularly located.

The inhaler of FIG. 3 also has a flat surface 80, that is an aid in holding the device when pressure is applied to either removable canister 40 or 50.

The embodiment of FIGS. 3 and 4 employs a different style cap that has an inner dimension of A″ that is larger than diameter B″ of the outlet nozzle 70 so that the cap can cover the outlet nozzle. The cap 65 also has a removable lid 90, which when removed allows the cap to be flipped and fitted on the outlet nozzle 70 in the opposite direction extending the length of the outlet nozzle.

To use the device depicted in FIG. 3, one removes the cap 65 from the outlet nozzle 70. Unlike the device of FIGS. 1 and 2, the unused canister of medication need not be covered. The embodiment of FIG. 3 is designed so that the removable canisters are angularly oriented toward each other at an angle o. This angular relationship allows the user to press down on the desired removable canister and the flat portion 8 of the housing causing a release of the desired medical aerosol spray. The housing contains a fluid communication release much the same as shown in FIG. 1. The pressurized medication is released and allowed to pass to and through the outlet nozzle. The undesired canister is untouched and thus remains unused.

To get a dose of the medication of the unused canister, the user switches ones hand grip and now holds the second canister and the flat surface 80. Then by applying pressure on the second canister a resulting release of medication is achieved.

As depicted in FIG. 4, the cap 65 can also be used as a mouthpiece spacer to extend the length of the outlet nozzle 70. By either removing the lid 90 of cap 65 or sliding it to the side, causing an open passage way, one is able to attach the spacer device to the outlet nozzle at the end where the lid 90 used to be, resulting in a desired extension of the outlet nozzle.

The embodiment of the invention a illustrated in FIGS. 5 and 6 depict an inhaler device similar to that of FIGS. 1 and 2. FIGS. 5 and 6, however, have a cover 100 that fits over the entire inhaler device 10. When removed, an insertable portion 110 of the cover 100 fits into an orifice 120 of the housing 10 to form an outlet nozzle. This device also has a removable cap 130 that fits over both canisters 40 and 50. During use, the cap 130 is placed over the unused canister and acts as a thumb hold, much in the same way as cap 60 was described in FIGS. 1 and 2. Both caps provide a space 135 to prevent the unused canister from being depressed into the device and releasing its medication. The cap also has a ledge 105 which is large enough to make contact with both ledges 32 or 22 of the housing 10 and the cover 100 when it is in an enclosed position as depicted in FIG. 5.

When the desired uncapped medication canister is depressed into the housing a similar fluid communication means as described in FIG. 1 releases the aerosol spray to and through the outlet nozzle.

In the embodiment of the invention, illustrated in FIGS. 7 and 8, the two canisters 40 and 50 and their respective chambers 20 and 30 are aligned in a "V" formation. Similar to the embodiment of FIG. 3, during application no cap is necessary to cover the unused canister. A thumb hold 180 acts as the alternative pressure point. The outlet nozzle 70 can be both retractable and extendable by movable portion 75.

Although the present invention has been described in conjunction with several preferred embodiments, it is to be understood that modifications and variations may be resorted to without departing from the spirit and scope of the invention, as those skilled in the art will readily understand. Such modifications and variations are considered to be within the purview and scope of the invention and appended claims.

What is claimed is:

1. An inhaler device comprising a housing having first and second chambers,
   said first chamber having a first internal compartment and a first removable canister of a first medication housed in said first compartment,
   said second chamber having a second internal compartment and a second removable canister of a second medication housed in said second compartment,
   said housing further having at least one common outlet nozzle in fluid communication with said canisters of medication, and means for independently allowing aerosol spray from either one of said first or second canisters to be discretely released through said common outlet nozzle.

2. An inhaler device as claimed in claim 1, further comprising a cap which removably covers said common outlet nozzle and said first and second removable canisters of medication.

3. An inhaler device as claimed in claim 2, wherein said cap when covering said removable canisters has an internal cavity sufficient to prevent any inward pressure on said covered canister.

4. An inhaler device as claimed in claim 1, wherein said common outlet nozzle is extendable.

5. An inhaler device as claimed in claim 1, wherein said common outlet nozzle is retractable.

6. An inhaler device comprising a housing having angularly oriented first and second chambers,
   said first chamber having a first internal compartment and a first removable canister of a first medication housed in said first compartment,
   said second chamber having a second internal compartment and a second removable canister of a second medication housed in said second compartment,
   said housing having a flat area between said angled first and second chambers,
   said housing further having at least one common outlet nozzle in fluid communication with said canisters of medication, and means for independently allowing aerosol spray from either one of said first or second canister to be discretely released through said common outlet nozzle.

7. An inhaler device as claimed in claim 6, further comprising a cap which removably covers said common outlet nozzle.

8. An inhaler device as claimed in claim 6, wherein said cap has a removable lid and is removably attachable to form an extension to said outlet nozzle.

9. An inhaler device as claimed in claim 6, wherein said common outlet nozzle is extendable.

10. An inhaler device as claimed in claim 6, wherein said common outlet nozzle is retractable.

11. An inhaler device comprising a housing having axially aligned first and second chambers,
    said first chamber having a first internal compartment and a first removable canister of a first medication housed in said first compartment,
    said second chamber having a second internal compartment and a second removable canister of a second medication housed in said second compartment,
    said housing having a removable cover,
    said housing further having a removable cap which covers said canister and is attachable to said removable cover,
    said cover is removably attachable to an orifice of said housing which includes an outlet nozzle,
    said outlet nozzle in fluid communication with said canisters of medication, means for independently allowing the dispersion of the contents of either of said first or second canisters through said common outlet nozzle.

* * * * *